US008835116B2

(12) United States Patent
Kennedy

(10) Patent No.: US 8,835,116 B2
(45) Date of Patent: *Sep. 16, 2014

(54) METHODS OF ANALYSIS OF ALLELIC IMBALANCE

(71) Applicant: Affymetrix, Inc., Santa Clara, CA (US)

(72) Inventor: Giulia Kennedy, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/667,998

(22) Filed: Nov. 2, 2012

(65) Prior Publication Data

US 2013/0190199 A1 Jul. 25, 2013

Related U.S. Application Data

(60) Continuation of application No. 13/222,851, filed on Aug. 31, 2011, now Pat. No. 8,323,894, which is a division of application No. 11/511,198, filed on Aug. 28, 2006, now Pat. No. 8,029,997, which is a division of application No. 10/321,741, filed on Dec. 16, 2002, now Pat. No. 7,097,976.

(60) Provisional application No. 60/389,745, filed on Jun. 17, 2002.

(51) Int. Cl.
*C07H 21/04* (2006.01)
*C12Q 1/68* (2006.01)
*C12N 15/10* (2006.01)

(52) U.S. Cl.
CPC ...... *C12N 15/1072* (2013.01); *C12Q 2600/158* (2013.01); *C12Q 1/6883* (2013.01); *C12Q 1/6886* (2013.01); *C12Q 1/6827* (2013.01)
USPC .......................... 435/6.11; 435/91.1; 435/91.2

(58) Field of Classification Search
None
See application file for complete search history.

(56) References Cited

U.S. PATENT DOCUMENTS

| | | | |
|---|---|---|---|
| 5,858,659 A | 1/1999 | Sapolsky et al. | |
| 6,013,449 A | 1/2000 | Hacia et al. | |
| 6,251,601 B1 * | 6/2001 | Bao et al. ............... | 435/6.14 |
| 6,303,301 B1 | 10/2001 | Mack | |
| 6,309,822 B1 | 10/2001 | Fodor et al. | |
| 6,361,947 B1 | 3/2002 | Dong et al. | |
| 6,368,799 B1 | 4/2002 | Chee | |
| 6,468,744 B1 | 10/2002 | Cronin et al. | |
| 7,097,976 B2 * | 8/2006 | Kennedy ............... | 435/6.11 |
| 8,029,997 B2 * | 10/2011 | Kennedy ............... | 435/6.1 |
| 8,323,894 B2 * | 12/2012 | Kennedy ............... | 435/6.1 |
| 2001/0007749 A1 * | 7/2001 | Feinberg ............... | 435/6 |

OTHER PUBLICATIONS

Mitsuya et al. (Human Molecular Genetics, vol. 8, No. 7, pp. 1209-1217, 1999).*
Killian et al. (Human Molecular Genetics, vol. 10, No. 17, pp. 1721-1728, 2001).*
Lee et al. (Nature Genetics, vol. 15, pp. 181-185, Feb. 1997).*
de los Santos (AJHG, vol. 67, No. 5, pp. 1067-1082, Nov. 2000).*
Choi J.D. et al., Microarray expression profiling of tissues from mice with uniparental duplications of chromosones 7 and 11 to identify imprinted genes. Mamalian Genome (2011) vol. 12, pp. 759-764.
Doherty et al., Biology Reproduction, vol. 62, pp. 1526-1535, 2000.
Enklaar et al., Genomics, vol. 67, pp. 179-187, 2000.
Falls et al., American Journal of Pathology, vol. 154, No. 3, Mar. 1999.
Lee et al. PNAS, vol. 96, pp. 5203-5208, Apr. 1999.
Lindblad-Toh K. et al., Loss-of-heterozygosity analysis of small-cell lung carcinomas using single nucleotide polymorphisms arrays. Nature Biotechnology, 2000, vol. 18, pp. 1001-1005.
McTernan et al., The Journal of Clinical Endocrinology & Metabolism, vol. 86, No. 10, pp. 4979-4983, 2001.
Mei R. et al., Genome-wide detection of allelic imbalance using human SNP's and high density DNA arrays. Genome Research, 2000, vol. 10, pp. 1126-1137.
Mizuno Y. et al., Asb4, Ata3 and Dcn are novel imprinted genes identified by high-throughput screening using RIKEN cDNA microarray. Biochem. Biophys. Res. Commun. 2002 vol. 290, Issue 5, pp. 1499-1505.
Morrison et al. "A catalogue of imprinted genes and parent-of-origin effects in humans and animals." Human Molecular Genetics, vol. 7, No. 10, pp. 1599-1609. 1998.
Weber et al., Extensive tissue-specific variation of allelic methylation in the Igf2 gene during mouse fetal development: relation to expression and imprinting. Mechanisms of Development, 2001, vol. 101, pp. 133-141.

* cited by examiner

*Primary Examiner* — Jeanine A Goldberg
(74) *Attorney, Agent, or Firm* — Banner & Witcoff, Ltd.

(57) ABSTRACT

Methods are provided for identification of genes that are imprinted. In another embodiment methods are provided for identification and analysis of genes whose expression shows allelic imbalance. The expression products transcribed from genes that are present in the genome as two or more alleles may be distinguished by hybridization to an array designed to interrogate individual alleles. Genes whose transcription products are present in amounts that vary from expected are candidates for allelic imbalance, imprinting and imprinting errors.

14 Claims, No Drawings

METHODS OF ANALYSIS OF ALLELIC IMBALANCE

RELATED APPLICATIONS

This application is a continuation of U.S. application Ser. No. 13/222,851, filed Aug. 31, 2011, which issued Dec. 4, 2012 as U.S. Pat. No. 8,323,894, which is a divisional of U.S. application Ser. No. 11/511,198, filed Aug. 28, 2006, which issued Oct. 4, 2011 as U.S. Pat. No. 8,029,997, which is a divisional of U.S. application Ser. No. 10/321,741, filed Dec. 16, 2002, which issued Aug. 29, 2006 as U.S. Pat. No. 7,097,976, which claims the benefit of U.S. Provisional Patent Application No. 60/389,745, filed Jun. 17, 2002, each of which is hereby incorporated herein by reference in its entirety for all purposes.

FIELD OF THE INVENTION

The invention relates to determining the imprinting status of genes. In one embodiment, the invention relates to identification of genes that are present in two allelic forms and show differential expression of the different alleles. The methods may be used to identify changes in imprinting status, to diagnose disease and to predict likelihood of disease. The present invention relates to the fields of molecular biology and genetics.

BACKGROUND

Each mammalian cell carries two copies of each gene, one inherited from the mother (on the maternal chromosome) and one inherited from the father (on the paternal chromosome). Most of the autosomal genes and X-linked genes in females are therefore biallelic i.e. both paternal and maternal alleles of the gene are expressed and the information of both copies is actively used in protein synthesis. In males, sex-linked genes are generally monoallelic since there is one X and one Y chromosome. Only a few genes on the Y chromosome have functional homologs on the X chromosome and are biallelic.

However, in humans and other mammals, monoallelic expression of biallelic genes has been demonstrated. These include genes on the inactive X-chromosome, genes encoding IL-2, IL-4, PAX-5, subunits of olfactory and lymphocyte receptors and imprinted genes. Allelic exclusion can result from two different mechanisms. The first mechanism is independent of the parental origin. One allele is randomly repressed and the pattern of allelic exclusion is transmitted stably to the daughter cells. This allelic exclusion can be due to X-chromosome inactivation, to programmed DNA rearrangement (B and T cell receptor in lymphocytes) or to other unknown mechanisms. The second mechanism, called genomic imprinting, is the result of a mark or imprint carried by a region of the chromosome and that reflects the parental origin. Imprinted genes in the mammalian genome are the genes for which one of the parental alleles is repressed whereas the other one is transcribed and expressed. Many imprinted genes are located in clusters and are associated with CpG-rich regions called CpG islands that are methylated uniquely on a specific parental chromosome (Razin A. and Cedar H. (1994) *Cell,* 77:473-476; Constancia M et al. (1998) 8:881-900, Reik W. and Walter J. (2001) *Nature Rev. Genet.,* 2:21-32 incorporated in their entity by reference for all purposes).

About sixty imprinted genes have been discovered in the mouse. An estimate of one to two hundred imprinted genes has been proposed based on mouse models (Barlow D. P. (1995) *Science,* 270: 1610-1613; Morison I. M. et al. (2001), *Nucl. Acids Res.,* 29:275-276 each of which is incorporated herein by reference in its entirety; databases available at http://www.otago.ac.nz/IGC and http://www.geneimprint-.com).

Imprinted genes tend to occur in clusters in both the human and mouse genomes (Reik W. and Walter J. (1998) *Curr. Opin. Genet.,* 8:154-164), which is incorporated herein by reference in its entirety. For example, in humans, two chromosomal regions (11p15.5 and 15q11-q13) harbor more than one imprinted gene. Some imprinted genes, such as Igf2 (Insulin-like growth factor type 2) and H19 (a non-coding RNA involved in silencing Igf2 expression) are located in imprinted clusters of genes that show coordinate regulation.

Imprinted genes can show monoallelic expression in some tissues and biallelic expression in others. For example, Igf2 is imprinted in most tissues but is biallelic in brain, liver and several other tissues. Monoallelic expression or disruption of monoallelic expression of some genes can lead to a disease phenotype. For instance, imprinting is a factor in an increasing number of genetic diseases such as Prader-Willi syndrome, Angelman syndrome, and Beckwith-Wiedmann syndrome. Imprinted genes and imprinting mechanisms are therefore important in human birth defects, cancer and in some neurological and psychiatric disorders (for review, see Falls G. J. et al. (1999) *Am. J. Path.,* 154:635-647).

Monoallelic expression of some genes that are present in two copies is required for normal development and viability. For example, human females have two copies of the X chromosome while males have a single X chromosome. However, females have effectively only a single copy of the X chromosome due to inactivation of one copy of the X chromosome in each cell. The inactive copy is known as a Barr body and inactivation is required for normal development. Inactivation of the X chromosome is random, resulting in mosaicism, meaning that in some cells the paternal copy of the X chromosome is inactivated and in some cells the maternal copy is inactivated. For genes that are present in a different allelic form on the paternal and maternal X chromosomes this results in expression of one allele in some cells and the other allele in other cells.

SUMMARY OF THE INVENTION

In one aspect methods are provided for identifying at least one heterozygous gene showing monoallelic expression in an individual. The method includes the steps of providing a genomic DNA sample from the individual; providing a nucleic acid array comprising probes designed to interrogate a plurality of polymorphisms; hybridizing the genomic sample to a first copy of the array; generating a hybridization pattern resulting from the hybridization; analyzing the hybridization pattern to determine the identity of the alleles present for at least one polymorphism in the plurality of polymorphisms; identifying at least one polymorphism in the plurality of polymorphisms that is heterozygous in the individual; isolating an RNA sample from the individual; hybridizing a nucleic acid sample derived from the RNA sample to the same array or to a second copy of the array and generating a hybridization pattern; and identifying at least one polymorphism in the plurality of polymorphisms that is heterozygous in the genome and homozygous in the RNA sample.

The polymorphisms may be single nucleotide polymorphisms. In some embodiments the polymorphisms are associated with a phenotype, for example a disease such as cancer or a neurological disorder like bipolar disorder or schizophrenia.

Monoallelic expression may be the result of imprinting and the parental origin of the expressed allele may be determined by establishing if the expressed allele is present in the maternal or paternal genome. Some imprinted genes express only the maternal copy of the gene and other imprinted genes express only the paternal copy of the gene. Imprinted genes may encode, for example, a lymphoid-specific factor, a subunit of an olfactory receptor, a subunit of a T cell receptor or a subunit of an immunoglobulin.

In many aspects, the samples derived from the genomic DNA and the RNA are differentially labeled. This allows both samples to be hybridized to the same array. Hybridization may be sequential or simultaneous where the sample may be mixed before or on the array. The differential labels allow separation of the hybridization patterns on the array. The nucleic acid samples that are hybridized may be genomic DNA or transcribed RNA that has been directly labeled, but in many embodiments the hybridized sample has been derived from the genomic DNA or transcribed RNA sample by, for example, amplification.

In one aspect, methods are provided for determining if the imprinting of a specific gene is tissue specific. The methods comprise the steps of identifying at least one heterozygous SNP in an imprinted gene in an individual; providing a nucleic acid array comprising probes designed to interrogate the SNP; isolating an RNA sample from each of a plurality of different tissue samples from the individual; hybridizing the RNA sample or a nucleic acid derived from the RNA sample from each tissue sample to an array to generate a hybridization pattern for each tissue sample; and analyzing the hybridization patterns to determine if the gene shows tissue specific imprinting.

In one aspect, methods are provided for determining if the imprinting of a specific gene is cell specific by comparing the expression of the gene in different cells of an individual. At least one heterozygous SNP on the DNA of an imprinted gene is identified; an RNA sample is isolated from a cell in which the gene is imprinted and from at least one different cell type; the RNA samples or a nucleic acid derived from the RNA samples are hybridized to a genotyping array and the hybridization pattern is analyzed to determine if the RNA is homozygous in both of the RNA samples. The RNAs from the different samples may be differentially labeled and hybridized to the same array either simultaneously or sequentially or they can be labeled with the same label and hybridized to separate arrays.

In one aspect, methods are provided for determining if the imprinting of a specific gene is species specific. The expression of the imprinted gene is analyzed in samples of the same tissue type from different species.

In one aspect, methods are provided for determining if the imprinting status of an imprinted gene is polymorphic in a population. The expression of the imprinted gene is compared between different individuals in a population. If the gene is imprinted in all of the individuals of the population it is not polymorphic in the population. If some individuals show imprinting of the gene, but other individuals do not, then the gene is identified as having a polymorphic imprinting status in that population.

In one aspect, imprinting is used to determine if a patient has an increased risk of developing a disease due to loss of imprinting. Heterozygous imprinted genes are identified in healthy individuals and these genes are analyzed in sample individuals to detect heterozygous genes that are imprinted in healthy individual but not imprinted in the patient.

In another aspect, a method is provided for determining if a preimplantation embryo has an increased risk of developing a disease due to abnormal imprinting.

In another aspect, a method is provided for identifying novel imprinted genes.

In another aspect, a method is provided for establishing a genome-wide imprinting chromosomal map. Genes that are heterozygous in the genome and homozygous in the expressed RNA are identified by hybridizing nucleic acid from genomic DNA and from transcribed RNA to an array that interrogates a plurality of SNPs. Chromosomal regions that carry two or more imprinted genes are identified on a genomic map. This mapping may be done, for example, for the human genome, for a specific tissue type, or for a specific developmental stage or stages. A genome-wide imprinting map may be used, for example, to identify genomic regions associated with disease.

In one aspect, methods are provided for assessing the genomic imprinting status of a cloned embryo. Cloning and nuclear cell transfer may result in abnormal imprinting and may result in abnormal phenotypes in cloned organisms. Imprinting in cloned individual may be compared with imprinting in normal individuals.

In one aspect, a method is provided for assessing the genomic imprinting status of genes from a transplantation tissue or cell.

In one aspect, a method is provided for identifying an agent that may cause imprinting deregulation in an individual, tissue or cell. The individual, tissue or cell is treated with the agent and imprinting is compared between treated and untreated samples.

DETAILED DESCRIPTION OF THE INVENTION

I. General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: *A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, *IRL Press*, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. No. 60/319,253, Ser. No. 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., PCR *Technology: Principles and Applications for DNA Amplification* (Ed. H. A. Erlich, Freeman Press, NY, N.Y., 1992); PCR *Protocols: A Guide to Methods and Applications* (Eds. Innis, et al., Academic Press, San Diego, Calif., 1990); Mattila et al., *Nucleic Acids Res.* 19, 4967 (1991); Eckert et al., PCR *Methods and Applications* 1, 17 (1991); PCR (Eds. McPherson et al., IRL Press, Oxford); and U.S. Pat. Nos. 4,683,202, 4,683,195, 4,800,159, 4,965,188,and 5,333,675, and each of which is incorporated herein by reference in their entireties for all purposes. The sample may be amplified on the array. See, for example, U.S. Pat. No 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., Science 241, 1077 (1988) and Barringer et al. *Gene* 89:117 (1990)), transcription amplification (Kwoh et al., *Proc. Natl. Acad. Sci.* USA 86, 1173 (1989) and WO88/10315), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), self-sustained sequence replication (Guatelli et al., *Proc. Nat. Acad. Sci. USA,* 87, 1874 (1990) and WO90/06995) and nucleic acid based sequence amplification (NABSA). (See, U.S. Pat. Nos. 5,409,818, 5,554,517, and 6,063,603, each of which is incorporated herein by reference). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($3^{rd}$ Ed. Cold Spring Harbor, N.Y., 2002); Berger and Kimmel *Methods in Enzymology*, Vol. 152, *Guide to Molecular Cloning Techniques* (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364, 731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

II. Definitions

An "individual" is not limited to a human being, but may also include other organisms including but not limited to mammals, plants, bacteria or cells derived from any of the above.

Nucleic acids according to the present invention may include any polymer or oligomer of pyrimidine and purine bases, preferably cytosine (C), thymine (T), and uracil (U), and adenine (A) and guanine (G), respectively. See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. A second nucleic acid sample may be derived from a first nucleic acid sample by any method known in the art. For example, a genomic DNA sample may be amplified by PCR or any other amplification method to generate a nucleic acid sample that is derived from the genomic DNA sample. RNA or cDNA may be made from a genomic DNA sample using methods known in the art.

An "oligonucleotide" or "polynucleotide" is a nucleic acid ranging from at least 2, preferably at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) or mimetics thereof, which may be isolated from natural sources, recombinantly produced or artificially synthesized and mimetics thereof. A further example of a polynucleotide of the present invention may be a peptide nucleic acid (PNA) in which the constituent bases are joined by peptides bonds rather than phosphodiester linkage, as described by Nielsen et al., *Science* 254:1497-1500 (1991), Nielsen , *Curr. Opin. Biotechnol.*, 10:71-75 (1999). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,599,695, 5,770,358, 5,789,162, 5,708,153, 6,040,193 and 5,800,992, which are hereby incorporated by reference in their entirety for all purposes.)

A "combinatorial synthesis strategy" is an ordered strategy for parallel synthesis of diverse polymer sequences by sequential addition of reagents which may be represented by a reactant matrix and a switch matrix, the product of which is a product matrix. A reactant matrix is a l column by m row matrix of the building blocks to be added. The switch matrix is all or a subset of the binary numbers, preferably ordered, between l and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Arrays may be packaged in such a manner as to allow for diagnostic use or can be an all-inclusive device; e.g., U.S. Pat. Nos. 5,856,174 and 5,922,591 incorporated in their entirety by reference for all purposes. Preferred arrays are commercially available from Affymetrix under the brand name GeneChip® and are directed to a variety of purposes, including genotyping and gene expression monitoring for a variety of eukaryotic and prokaryotic species. (See Affymetrix Inc., Santa Clara and their website at affymetrix.com.).

Complementary or substantially complementary refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are the to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization".

"Hybridization conditions" will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the thermal melting point (Tm) of the specific sequence at a defined ionic strength and pH. The Tm is the temperature (under defined ionic strength, pH and nucleic acid composition) at which 50% of the probes complementary to the target sequence hybridize to the target sequence at equilibrium. Typically, stringent conditions include salt concentration of at least 0.01 M to no more than 1 M Na ion concentration (or other salts) at a pH 7.0 to 8.3 and a temperature of at least 25° C. For example, conditions of 5X SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above.

"Hybridization probes" are oligonucleotides capable of binding in a base-specific manner to a complementary strand of nucleic acid. Such probes include peptide nucleic acids, as described in Nielsen et al., *Science* 254:1497-1500 (1991), Nielsen *Curr. Opin. Biotechnol.*, 10:71-75 (1999) and other nucleic acid analogs and nucleic acid mimetics. See U.S. Pat. No. 6,156,501 filed Apr. 3, 1996.

"Hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

A "probe" is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

A "target" is a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

An "isolated nucleic acid" is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

"Mixed population" or "complex population" refers to any sample containing both desired and undesired nucleic acids. As a non-limiting example, a complex population of nucleic acids may be total genomic DNA, total RNA or a combination thereof. Moreover, a complex population of nucleic acids may have been enriched for a given population but includes other undesirable populations. For example, a complex population of nucleic acids may be a sample which has been enriched for desired messenger RNA (mRNA) sequences but still includes some undesired ribosomal RNA sequences (rRNA).

"RNA" or "transcribed RNA" as used herein, include, but are not limited to RNA transcripts, pre-mRNA transcript(s), transcript processing intermediates, mature mRNA(s) ready for translation and transcripts of the gene or genes, or nucleic acids derived from the RNA transcript(s). Transcript processing may include splicing, editing and degradation. Expressed RNAs may be mRNAs that code for a protein or non-coding RNAs. Non coding RNA (ncRNA) refers to all RNAs that are not messenger RNAs (mRNA). Although most genes are transcribed into messenger RNA that encode proteins, ncRNA genes generate transcripts lacking protein-coding potential (e.g. Functional RNA (fRNA), Micro RNA (miRNA), Ribosomal RNA (rRNA), Small Interfering RNA (siRNA), Small Nuclear RNA (snRNA), Small non-mRNA RNA (snmRNA), Small nucleolar RNA (snoRNA), Small temporal RNA (stRNA), Transfer RNA (tRNA)—For review See Eddy SR, Nature Reviews Genetics, 2:919, 2001). The ncRNAs may function at a regulatory, catalytic or structural level. Several non-coding RNA genes have been found to be imprinted or included in imprinted domains and implicated in regulating the imprinted expression of coding transcripts (e.g. H19, AIR, XIST, Rian, DGCR5, IPW, GNAS1, ZNF127-AS, PAR-SN, PAR-1, PAR-5, UBE3A-AS, KvDMR-1). As used herein, a nucleic acid derived from an RNA transcript refers to a nucleic acid for whose synthesis the RNA transcript or a subsequence thereof has ultimately served as a template. Thus, a cDNA reverse transcribed from an mRNA, a cRNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. An RNA sample includes, but is not limited to, RNA transcripts of the gene or genes and any nucleic acid sample derived from the RNA, such as, cDNA reverse transcribed from the RNA, cRNA transcribed from the cDNA, DNA amplified from the RNA, RNA transcribed from amplified DNA, and the like. Likewise a genomic DNA sample includes isolated genomic DNA and any nucleic acid sample derived from the isolated genomic DNA, such as, isolated genomic DNA that has been fragmented and labeled, as well as nucleic acid samples derived from the isolated genomic DNA, such as amplified double or single stranded fragments of the isolated genomic DNA, RNA transcribed from the amplified DNA, and the like. The genomic DNA sample contains sequence information that represents the information content of the genome and the RNA sample contains sequence information that represents the information content of the transcribed RNA.

A "fragment", "segment", or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, New York (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

"Restriction enzymes" recognize in general a specific nucleotide sequence of four to eight nucleotides (through this number can vary) and cut a DNA molecule at specific site. For example, the restriction enzyme EcoRI recognized the sequence GAATTC and will cut the DNA between the G and the first A. Many different restriction enzymes can be chosen for a desired result (For description of many restriction enzymes, see, New England BioLabs Catalog which is herein incorporated by reference in its entity for all purposes). Methods for conducting restriction digests will be known to those skilled in the art. For thorough explanation of the use of restriction enzymes, see for example, section 5, specifically pages 5.2 to 5.32 of Sambrook et al., incorporated by reference above. This method can be used for complexity management of nucleic acid samples such as genomic DNA, see U.S. Pat. No. 6,361,947, which is hereby incorporated by reference in its entirety.

"In silico digestion" is a computer-aided simulation of enzymatic digests accomplished by searching a sequence for restriction sites. In silico digestion provides for the use of a computer system to model enzymatic reactions in order to determine experimental conditions before conducting any actual experiments. An example of an experiment would be to model digestion of the human genome with specific restriction enzymes to predict the sizes of the resulting restriction fragments.

A primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

A "genome" is all the genetic material in the chromosomes of an organism. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. A genomic library is a collection of clones made from a set of randomly generated overlapping DNA fragments representing the entire genome of an organism.

An "allele" refers to one specific form of a gene within a cell or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

At each autosomal specific chromosomal location or "locus" an individual possesses two alleles, one inherited from the father and one from the mother. An individual is "heterozygous" at a locus if it has two different alleles at that locus. An individual is "homozygous" at a locus if it has two identical alleles at that locus.

"Polymorphism" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Single nucleotide polymorphism (SNPs) are positions at which two alternative bases occur at appreciable frequency (>1%) in the human population, and are the most common type of human genetic variation. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

"Genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. A genotype may be the identity of the alleles present in an individual at one or more polymorphic sites.

"Genomic imprinting" or "allelic exclusion according to parent of origin" is a mechanism of gene regulation by which only one of the parental copies of a gene is expressed. Paternal imprinting means that an allele inherited from the father is not expressed in offspring. Maternal imprinting means that an allele inherited from the mother is not expressed in offspring. Imprinted genes are the genes for which one of the parental alleles is repressed whereas the other one is transcribed and expressed. The expression of an imprinted gene may vary in different tissues or at different developmental stages. Imprinted genes may be expressed in a variety of tissue or cell types such as muscle, liver, spleen, lung, central nervous system, kidney, testis, ovary, pancreas, placenta, skin, adrenal, parathyroid, bladder, breast, pituitary, intestinal, salivary gland blood cells, lymph node and other known in art. For instance, Igf2 imprinting results in repression of the maternally-derived allele in most tissues except brain, adult liver and chondrocytes (Vu T. H. and Hoffman A. R. (1994) Nature, 371:714-717, UBE3A (ubiquitin protein ligase 3) is paternally repressed exclusively in brain, KCNQ1 is paternally repressed in most tissues but is not imprinted in heart and WT1 (Wilms' tumor gene) is paternally repressed in cells of placenta and brain but not in kidney.

Genes may be imprinted only during specific developmental stages of an organism. For example, PEG1/MEST is maternally repressed in fetal tissue but biallelically expressed in adult blood. Also, genes may be paternally or maternally repressed in a particular species (e.g. murine versus human, Killian K. J. et al. (2001) *Hum. Mol. Genet.*, 10:1721-1728). Loss of imprinting or LOI is said to occur when the normally silenced allele of an imprinted gene is activated. Both alleles of a gene that is usually imprinted may be expressed at equal levels.

Degree of allelic imbalance refers to the differential expression of the two alleles of a gene for which imprinting is assessed (i.e. maternal versus paternal: M/P). RNA is typically transcribed from maternal and paternal genes equally (i.e.50/50). Imprinting is an example where either the maternal or paternal allele is transcribed and corresponds to a 100/0 or 0/100 expression ratio. Allelic imbalance is found when one parent is preferentially transcribed more than the other (e.g. 80/20).

The diseases caused by imprinting, abnormal imprinting such as LOI, and monoallelic expression include, but are not limited to, Prader-Willi syndrome, Angelman syndrome, Beckwith-Wiedmann syndrome, Silver-Russel syndrome, cancers, sudden infant death syndrome, birth defects, mental retardation, diabetes and gestational diabetes, neurological disorders, autism, bipolar affective disorder, epilepsy, schizophrenia, Tourette syndrome and Turner syndrome.

The term "gene expression" refers to the process in which genetic information flows from DNA to functional molecule, such as protein or RNA molecules. Monoallelic expression refers to the expression of only one of the two alleles of the gene in a cell, because of imprinting, X-inactivation, or gene rearrangements that take place within immunoglobulin and T-cell receptor genes.

Analysis of monoallelic expression of genes in an individual can be performed on a biological sample. Example of tissue or cells from which RNA can be extracted and analyzed includes, but is not limited to, skin, ligaments, eye, kidney, liver, heart, lung, bone-marrow, neural tissue, motor neurons, sensory neurons, blood-white cells and other myelocyte lineage and muscle.

The term "imprinting map" illustrates the chromosomal regions of the genome subject to imprinting. Chromosomes that are likely to show imprinting include 2, 6, 7, 11, 14, 15, 16, 20 and X (Ledbetter D. H. and Engel E. (1995) Hum. Mol. Genet. 4: 1757; Morison I. M. and Reeve A. E. (1998) Hum. Mol. Genet. 7: 2599). Chromosome regions could be labeled according to the phenotype (i.e. M for maternal when no paternal allele is expressed or P for paternal when no maternal allele is expressed).

III. The Process a. Methods to Identify Imprinted Genes

In general methods are provided for determining if both alleles of a heterozygous gene are being expressed. Diploid organisms generally have two copies of each gene, but both copies are not always expressed at equal levels and in some circumstances only one of the copies is expressed. For many genes this allelic imbalance is required for normal development and a deleterious phenotype results when the imbalanced regulation is altered. Imprinted genes provide multiple examples where it is important that only one copy of the gene be expressed. Allelic imbalance may be regulated developmentally or in a tissue specific manner or it may be constitutive. To determine if both alleles of a heterozygous gene are being expressed the hybridization pattern resulting from the genomic DNA.

Several methods have been used to determine imprinted genes (For review see, Oakey R. J. and Beechey C. V. (2002), *Trends Genet.*, 18:359-366; Kelsey G. and Reik W. (1998), *Methods*, 14:211-234). These methods include subtractive hybridization (Kuroiwa Y. et al. (1996) *Nat. Genet.*, 12:186-190; Kaneko-Ishino Y. et al. (1995), *Nat. Genet.*, 11:52-59; Kagitani F. et al. (1997), *Nucleic Acids Res.*, 25:3428-3432; Piras .G et al. (2000), *Mol. Cel. Biol.*, 20:3308-3315), differential display PCR (Hagiwara Y. (1997), Proc. Natl. Acad. Sci. U.S.A, 94:9249-9254; Georgiades P. et al., *Development*, 127: 4719-4728; Takada S. (2000), *Curr. Biol.*, 10:1135-1138), serial analysis of gene expression (Velculescu V. E. (1995), *Science*, 270:368-369; Velculescu V. E. (2000), *Trends Genet.*, 16:423-425), microarrays (Choi J.D. (2001), *Mamm. Genome*, 12:758-764; Kobayashi S. (2000), *Genes Cells*, 5:1029-1037; Mizuno Y. (2002), *Biochem. Biophys. Res. Commun.*, 290:1499-1505), antisense and non-coding RNAs (Lehner B. (2002), *Trends. Genet.*, 18:63-65) and single nucleotide polymorphisms (Coghill E. L. (2002), *Nat. Genet.*, 30:255-256; Uejima H et al. (2000), *Nat. Genet.*, 25: 375-376).

The methods of the present invention provide a systematic approach to study whole genome allelic exclusion. In some embodiments genes that are heterozygous in the genome are analyzed to determine if the RNA transcribed from that gene comes from one allele or both alleles of the gene. Heterozygous genes that are expressed with an allelic imbalance may be identified. Rapid, efficient and scalable methods to identify imprinted genes are included. Genes that display errors in imprinting may also be identified. In another embodiment arrays for carrying out this analysis are disclosed. Imprinting and errors in imprinting may be tissue specific or may be present only during specific developmental stages. In some embodiments the method may be used to screen more than 100, 1000, 5000, 10,000, 50,000 or 100,000 genes.

Both the silent and the active parental alleles of an imprinted gene may be retained in the genome. To determine if a gene is imprinted nucleic acid samples from an individual may be characterized at both the genomic and the transcriptional levels. A gene that is imprinted may be present in two allelic forms in the genome but only one of the alleles is transcribed, resulting in the detection of both alleles in the genomic sample but only one of the alleles in the transcribed RNA. In some embodiments SNPs, within the transcribed regions of a gene, are used to determine if multiple alleles of a gene are present in the genome and to monitor the expression of the different allelic forms of the gene. Microarrays designed to interrogate polymorphisms may be used to identify the presence or absence of individual SNP alleles in genomic DNA or in transcribed RNA (see, for example, U.S. patent application Ser. Nos. 09/916,135 and 10/264,945). The methods may be used to determine if only the paternal allele is expressed, if only the maternal allele is expressed or if both alleles are expressed. For example, if the individual is AB, carrying both the A and B alleles, the A allele being the maternal copy and the B allele being the paternal copy, but only the A allele is detected in the RNA then the gene may be imprinted with the paternal copy being silent and the maternal copy being expressed. If both the A and B alleles are present in the RNA the gene displays biallelic expression and is not imprinted. If only the B allele is present in the RNA then the maternal allele is silent and only the paternal allele is expressed.

The parental origin of an imprinted allele may also be determined. If an organism is AB at a given SNP in an imprinted gene and at least one of the parents is homozygous the methods may be used to determine the parental origin of the expressed allele. For example, if the expressed allele is B and the mother was AA and the father BB then the silenced allele is the maternal allele, the A allele, and the expressed allele is the paternal allele, the B allele. The parental origin of an imprinted allele may effect the penetrance and severity of diseases associated with imprinting.

In some embodiments both alleles are present in the RNA but one allele is present at higher levels than the other allele. This allelic imbalance may be detected by the present methods.

Single nucleotide polymorphisms (SNPs) may be used for testing human genetic variation. SNPs are present in the genome in a high density, they are stable mutations relative to other markers such as microsatellites and they may be analyzed using high throughput typing methodologies which may be relatively inexpensive. Since SNPs are the most abundant form of human genetic variation, they are useful markers for genomic research (Collins F. S. et al., (1996) *Science*, 278:1580-1581; Wang D. G. et al. (1998), *Science*, 280:1077-1082; Gray I. C. et al. (2000), *Hum. Mol. Genet.*, 9:2403-2408). On average, SNPs occurs every 1,000 bases when two human chromosomes are compared (The International SNP Map Working Group, *Science*, 409:928-933, 2001). Strategies for detection and identification of polymorphisms are described in U.S. Pat. Nos. 5,858,659, 6,361,947, U.S. patent application Ser. Nos. 09/916,135, 09/920,491, 09/910,292, 10/264,945 and 10/013,598, and Dong et al. (2001), *Genome Res.*, 11:1418-1424, each of which is incorporated by reference in their entity for all purposes. Some embodiments of the present methods employ pre-characterized SNPs. That is, genotyping may be performed after the location and the nature of polymorphic forms at a site have been determined. Genotyping arrays may be designed to analyze many different polymorphisms simultaneously, for example, an array may be designed to interrogate 1000, 5,000, 10,000, or 20,000 to 10,000, 20,000, 100,000, 500,000, or 1,000,000 different polymorphic positions.

In some embodiments a genomic DNA sample or a nucleic acid sample derived from genomic DNA is hybridized to a genotyping array and one or more heterozygous SNPs are identified. SNPs that are heterozygous in the genomic DNA may then be analyzed to determine if RNA transcribed from that region is homozygous or heterozygous. The analysis of the transcribed RNA may be by hybridizing the transcribed RNA or a nucleic acid sample derived from the transcribed RNA to a genotyping array. In order to determine if one or more heterozygous SNPs are homozygous in the transcribed RNA the RNA may be converted to cDNA and hybridized to a second copy of the array. In some embodiments the cDNA is further amplified. In some embodiments the transcribed RNA is labeled directly and hybridized directly to an array. Methods for amplification and labeling are described above and in U.S. patent application Ser. Nos. 09/285,658, 09/961, 709, 10/090,320 and 09/738,892. The gene is identified as an imprinted gene if the SNP is heterozygous in the genomic DNA but homozygous in the RNA.

In some embodiments genes that are known to be imprinted are analyzed to detect failure of imprinting or improper imprinting. For example, some genes are normally expressed only from the maternal allele and expression from both maternal and paternal alleles results in an abnormal or disease phenotype. If the individual is heterozygous at that location the expression products from each allele may be detected by hybridization to a genotyping array. In some embodiments the amount of RNA resulting from each allele may be determined. An approximately equivalent amount of expression is expected from each allele.

In some embodiments the genomic DNA and the RNA or their amplification products bear different labels and are hybridized simultaneously to the same array, meaning the same copy of an array. In some embodiments the samples may be labeled with the same label and each sample may be hybridized to a different copy of the same array. The samples may be differentially labeled so that the signal resulting from the genomic DNA and the signal resulting from the RNA may be distinguished (i.e. two color labeling). A variety of different fluorescent labels are available and may be used. For example, one sample can be labeled with fluorescein and the other with biotin, which can be stained with phycoerythrin-steptavidin after hybridization (See U.S. Pat. Nos. 6,013,449 and 6,309,822, which are both incorporated herein by reference in their entireties).

For assay of genomic DNA, virtually any biological sample (other than pure red blood cells) is suitable. For example, convenient tissue sample include whole blood, saliva, buccal, tears, semen, urine, sweat, fecal material, skin and hair. The invention analyses sequentially or simultaneously the polymorphic forms of the RNA transcript. In general, the same probe arrays that are used for analyzing polymorphic forms in genomic DNA can be used for analyzing polymorphic forms for transcripts, for example the Human 10K Mapping Set, (Affymetrix, Santa Clara). RNA for analysis is isolated from a biological tissue or fluid or cells in which the gene of interest is expressed. Sample includes sputum, blood, blood cells (e.g., white cells), tissue or fine needle tissue samples, urine, peritoneal fluid and pleural fluid, or cells therefrom. Biological samples may also include sections of tissues such as frozen sections taken from histological purposes. Methods for isolating mRNA are described in Chapter 3 of *Laboratory techniques in Biochemistry and Molecular Biology: Hybridization With Nucleic Acid Probes, Part I. Theory and Nucleic Acid Preparation*, P. Tijssen, ed. Elsevier, N.Y. (1993). For example total RNA is isolated from a given sample using acid-guanidium-phenol-chloroform extraction method and polyA$^+$ mRNA is isolated by oligodT column chromatography or by using $(dT)_n$ magnetic beads (see, e.g., Sambrook et al., *Molecular Cloning: A Laboratory Manual* ($2^{nd}$ ed.), Vol. 1-3, Cold Spring Harbor Laboratory (1989))

Methods of genotyping using a nucleic acid array following complexity reduction have been described, for example, in U.S. Pat. Nos. 6,361,947 and U.S. patent application Ser. No. 09/916,135, also see, Dong S. et al. (2001), *Genome Res.*, 11:1418-1424, each of which are incorporated herein by reference in their entireties. In brief, this method comprises fragmenting nucleic acids sample to form fragments, ligating adaptors to the fragments and amplifying the fragments under conditions that favor amplification of fragments of a particular size. In silico digestion is used in many embodiments to predict the SNPs that will be present when a genome is digested with a particular restriction enzyme or enzymes. The SNPs and corresponding fragment sizes can be further separated by computer into subsets according to fragment size. The information is then used to design arrays to interrogate SNPs predicted to be present in a particular size fraction resulting from a particular digestion and amplification method. Arrays may be designed to interrogate a particular subset of sequences or fragments that may include a subset of polymorphisms. In some embodiments a subset of a genome is isolated by, for example, preferential amplification of a subset of fragments. In some embodiments the subset of fragments that is preferentially amplified are those fragments that are of a selected size range, for example, between 1, 200, 400, 500, or 1,000 and 800, 1,000, 2,000 or 5,000 bases. In many embodiments the array is designed to interrogate one or more polymorphic positions predicted to be present in the fragments of the subset of fragments isolated or amplified. In some embodiments SNPs are amplified by target specific amplification using one or more primers that hybridize near the SNP or interest. A collection of SNPs may be amplified using a collection of target specific primers. The array may be designed to interrogate the SNPs in the collection of SNPs.

In one embodiment, mRNA is extracted from different tissues or from the same tissue at different developmental stages for example adult brain, adult liver, fetal brain, fetal liver. In some embodiments imprinting that is developmentally regulated or regulated in a tissue specific manner may be identified. Genomic DNA and mRNA are genotyped and are compared in order to identify imprinted genes that are tissue specific or that are developmentally regulated. To confirm or detect tissue or developmental regulation of imprinting, an individual whose genomic DNA is heterozygous for a SNP is identified and RNA is analyzed to determine if the gene shows monoallelic or biallelic expression in different tissues or at different developmental stages. For example, the following comparisons are made: 1) fetal brain versus adult brain, 2) fetal liver versus adult liver, 3) adult brain versus adult liver, 4) fetal brain versus fetal liver. Using this method one can produce a representation of the genes imprinted in the major organs of an individual at different developmental stages. Imprinting in an individual may be compared to the imprinting expected in a normal sample.

In one embodiment, analysis of imprinting genes is performed on tissues or cells to be used for transplantation in order to avoid the possibility of increasing the disease risk in the transplant recipient.

Another aspect of the invention is the creation of a genome-wide chromosomal imprinting map. One embodiment describes a method of identifying imprinted genes by screening a large number of genes. In one embodiment, gene(s) within 2 to 4 million base pairs of a known imprinted gene is identified and assayed whether it is uniparentally expressed or not. Imprinted genes are indeed often clustered in large domains. For instance, studies have identified a set of novel imprinted genes within 1.5 Mbases of chromosome 15q (implicated in Prader-Willi syndrome and Angelman syndrome. (See, Lee S. and Wevrick R. (2000) *Am. J. Hum. Genet,*. 66:848-858). In one embodiment a human chromosomal imprinting map is established. This map has important clinical implications, particularly in the area of prenatal diagnosis. In one embodiment, it is determined if these newly identified imprinted genes are associated with a disease state. One embodiment describes arrays displaying oligonucleotides probes for interrogating genes imprinted in different tissues and/or at different developmental stages. In another embodiment, oligonucleotide arrays are used to interrogate imprinted genes in different species.

b. Correlation of Imprinted Genes With Phenotypic Characteristics

In some embodiments errors in imprinting may be correlated with phenotype. Correlation may be used to assess risk for disease, predict response to environment, predict treatment outcome or to determine the impact of cloning on imprinting.

Imprinted genes that correlate with disease are particularly interesting because they represent mechanisms to accurately diagnose syndromes related to genomic imprinting. Several genetic changes are known to disrupt the expression of imprinted genes. Large deletions on the chromosome containing the active allele can disrupt or delete the expressed copy of an imprinted gene causing loss of function. Uniparental disomy, a duplication of one allele with loss of the other, may result in loss of function if the inactive allele is duplicated.

A significant proportion of imprinted genes have been shown to be implicated in the control of fetal growth. Some diseases such as Prader-Willi syndrome (Nicholls R. D. and Knepper J. L. (2001), *Annu. Rev. Genomics Hum. Genet.,* 2:153-175), Angelman syndrome (Rougelle C. et al. (1997), *Nat. Genet.,* 17:14-15), Silver-Russel syndrome (Hitchins M. P. et al. (2001), *Eur. J. Hum. Genet.,* 9:82-90) and Beckwith-Wiedmann syndrome have been correlated with imprinting mechanism (for review see, Falls G. J. (1999) *Am. J. Path.,* 154:635-647). Parent-of-origin inheritance effects, i.e. occurrence or severity of the symptoms, suggest that imprinted genes are also implicated in autism, bipolar affective disorder, epilepsy, schizophrenia, Tourette syndrome and Turner syndrome. Also, it has been shown that some tumors are linked with the preferential loss of a particular parental chromosome, indicating the involvement of imprinted genes. Imprinted genes implicated in human carcinogenesis include Igf2, WT1, p57$^{KIP2}$, p73, NOEY2 and M6P/Igf2R (for review, see Fall G. J. et al. (1999), *Am. J. Path.,* 154:635-647). Loss of imprinting (LOI) in cancer can lead to activation of normally silent alleles of growth-promoting genes (Rainier et al. (1993) *Nature* 362: 747). This phenomenon has been observed in various adult cancers including lung, breast, gastrointestinal, esophageal, endometrial, uterine, ovarian, cervical, skin, endocrine, urinary, prostate, colorectal cancers and in leukemia and lymphoma (For review, see Jirtle R. L. (1999) *Exp. Cell Res.,* 248:18-24). LOI may be used to diagnose or predict risk of certain diseases such as colon cancer. In some embodiments LOI is monitored in response to treatment to determine if LOI is impacted or reversed. Monitoring of LOI may be used to evaluate candidate drugs or treatments for ability to reverse LOI.

In one embodiment, individuals are tested for the presence or the absence of an imprinted gene and for the phenotypic trait or traits of interest. The presence or absence of imprinting in individuals that exhibit a particular phenotype is compared to imprinting of the same gene in individuals who lack the phenotype to determine if the presence or absence of imprinting in a particular gene or genes is associated with the phenotype.

In another embodiment the methods of the invention provide a method to determine whether the imprint status at a particular locus is polymorphic. Some imprinted genes such as Igf2, WT1, HTR2A appear to be polymorphic, the gene being imprinted in some individuals but not in others or imprinted in humans but not in other species such as in mouse (Killian K. J. et al. (2001) *Hum. Mol. Genet.,* 10:1721-1728). It is not known yet if polymorphic imprinting can determine individual and/or species differences in susceptibility to disease.

In some embodiments, the methods of the invention may be used to evaluate the environmental influence of physical, chemical or radiation agents on the imprinting status of the genome and assess how it is related to known diseases or phenotypes. Since DNA methylation and chromatin structure are important in regulation of genomic imprinting, environmental factors capable of causing epigenetic changes in DNA can potentially alter the expression of imprinted genes resulting in genetic diseases including cancer and behavioral disorders (Murphy S. K. and Jirtle R. L. (2000) *Environ. Health Perspect.,* 108 (Suppl.1): 5-11). In another embodiment the methods may be used to correlate imprinting with exposure of an individual or an individual's parents to a stress, such as a chemical mutagen. For example, a correlation has been found between parental exposure to chemical mutagens and the occurrence of Prader-Willi syndrome in children (Cassidy S. B. et al. (1989) *Am. J. Hum. Genet.,* 44:806-810).

Cloning of various mammalian organisms has been achieved by nuclear transfer technology: a nucleus is removed from a somatic donor cell and is transplanted in an enucleated oocyte (for review see, Gurdon J. B. and Colman A. (1999) *Nature,* 402:743-746). The renucleated oocyte will carry the genome of only the donor individual and if implanted will develop to a cloned individual genetically similar to the nuclear donor. Cloning in mammals is very inefficient since less than 1% of the clones survive to term. Most of those who survive develop severe abnormalities (such as fetal overgrowth, enlarged heart, placental overgrowth, defective kidneys, immature lung development, reduced immunity to disease . . . ) and die soon thereafter (Young L. E. et al. (1998) *Rev. Reprod.,* 3:155-163). Fetal over growth or large offspring syndrome is a major problem encountered in cloning and is believed to result from parental genomic imprinting (Young L. E. et al. (2001) *Nat. Genet.,* 27:153-154). Imprinted genes are switched off in the embryo and many of them belong to the fetal growth pathway. For instance, paternal imprinted genes tend to enhance fetal growth (such as Igf2) whereas maternal imprinted genes (such as H19) tend to suppress fetal growth. The genome-wide balance in the dosage of theses factors determines the size of the offspring.

Imprinting poses a potential problem for cloning by nuclear transfer. To be successful in directing development, an adult nucleus would have to have maintained a stable imprinting pattern and this pattern would need to be preserved or replaced following nuclear transfer. The success of producing live-born animals by this procedure suggests that such issues are not insurmountable, but there may be imprinting errors that contribute to the high failure rate seen in cloning experiments to date. In some embodiments of the present invention methods are provided for determining if a cloned individual has a normal imprinting pattern for one or more genes. The methods may also be used to identify genes that show imprinting during one stage of development but not during another stage of development.

In some embodiments, imprinted gene expression patterns are compared between clones and normal embryos. It has been shown that the level of expression of imprinted genes such as Igf2R can vary significantly in cloned embryos that are cultured in vitro before implantation (Young L. E. et al. (2001) *Nat. Genet.,* 27:153-154). Preimplantation culture conditions can influence the regulation of growth-related imprinted genes (Khosla S. et al. (2001) *Biol. Reprod.,* 64:918-926). Loss of imprinting during embryo culture could also account to the reduced birth weight of progeny resulting from human in vitro fertilization. Moreover, two children conceived by intracytoplasmic sperm injection have been shown to develop Angelman syndrome due to a sporadic imprinting defect (Cox G. F. et al. (2002) *Am. J. Hum. Genet.,* 71:162-164). In order to obtain and improve the success rate of obtaining viable and healthy progeny using cloning methods, it is essential to examine and evaluate the expression of the imprinted genes before implantation in the uterus. In some embodiments, expression of imprinted genes is assayed in embryos at different key stages of development prior to implantation in the uterus. In another embodiment preimplantation embryos are diagnosed for any known disease correlated with imprinted genes. In another embodiment a cloned tissue or organism is assessed for imprinting of one or more genes.

In some embodiments the methods are used to determine the imprinting status of genes in cells derived from stem cells prior to use of these cells for cloning or prior to transplantation of tissue derived from embryonic stem cells into a patient. Stem cells such as embryonic germ cells (EG cells) or embryonic stem cells (ES cells) are pluripotent cells that can differentiate into any cell type. Stem cell derived tissues have the potential to be used for transplantation therapy to replace damaged differentiated cells or cells lost in many disorders such as diabetes mellitus (to replace insulin-secreting beta cells of the pancreas) and Parkinson's disease (to replace dopamine secreting cells of the brain). However, work on embryonic stem cells and tissues derived from stem cells indicates that these methods may introduce imprinting errors that might result in a disease phenotype in the individual. From this perspective, it is important to be able to check the expression of imprinted genes in stem cell derived tissues before transplantation.

Errors in silencing of genes on the X-chromosome may also be detected by comparing the genotype of multiallelic loci and the expressed RNA. X-chromosome inactivation is random so in some cells the maternal copy will be inactivated while in other cells the paternal copy will be inactivated. The methods may be used to determine which copy of the X-chromosome is inactivated in a given cell by comparing the RNA expressed in the cell with the genotype of the maternal and paternal X chromosomes for at least one heterozygous gene.

EXAMPLES

Reference will be now made in detail to illustrative embodiments of the invention. While the invention will be described in conjunction with the illustrative embodiments, it will be understood that the invention is not limited. On the contrary, the invention is intended to cover alternatives, modifications and equivalents, which may be included within the spirit and scope of the invention. The following example is intended to illustrate the invention.

Example 1

Identification of Imprinted Genes in an Individual

A total of 5 μg of human genomic DNA is digested with restriction enzyme, in 1× restriction enzyme buffer for 2 hours at 37° C. Heating the reaction at 70° C. for 20 minutes inactivates restriction enzyme. The digestion fragments are then ligated with adaptors with 8 mM DTT, 1 mM ATP and 5000 units T4 DNA ligase at 16° C. for 2 hours. The reaction is stopped by heating the mixture for 10 minutes at 70° C. Fragments are then amplified by PCR with 5 μM of the appropriate primers in 250 μM dNTPs, 15 mM Tris-HCl pH 8.0, 2 mM $MgCl_2$ and 5 units of TaqGold polymerase. An aliquot of the PCR product is analyzed on an agarose gel to confirm that the products have the correct average size. The PCR fragments are segmented with DNase I by incubation for 20 minutes at 37° C. and then 10 minutes at 95° C. DNA is labeled by mixing the fragmented DNA with biotin-$N^6$-ddATP and terminal transferase for 2 hours at 37° C. DNA fragments are heat denatured by boiling for 30 minutes. Denatured enzymes are removed by centrifugation. Standard procedures are used for hybridization, washing, scanning and data analysis. PCR products are hybridized to an array designed to detect the presence or the absence and the heterozygosity status of a given SNP containing target in the sample. After hybridization, the array is washed and stained with Streptavidin-R-phycoerythrin conjugate and washed on a fluidics station (Affymetrix). Anti-Streptavidin antibody is then added and the array is stained again with the staining solution followed by washing as in the previous step. The arrays are then scanned with a chip scanner at 570 nm. A first hybridization pattern is obtained. Single nucleotide polymorphisms that are heterozygous in the genomic DNA are identified.

Total RNA is isolated from a specific tissue at a specific developmental stage. Total mRNA is purified by oligo(dT) column chromatography or by using (dT) magnetic beads. Poly(A)+ mRNA is generated and reverse transcribed with a reverse transcriptase (Superscript II system, Life Technologies, Rockville, Md.). RNA is removed by using RNase H and RNase A for 10 minutes at 37° C. The cDNA is purified using the Quiaquick PCR purification kit from Quiagen (Valencia, Calif.). Before hybridization the cDNA is fragmented using a partial DNase I digest or by incubating RNA in RNase free RNA fragmentation buffer (200 mM Tris-acetate pH 8.1; 500 mM potassium acetate, 150 mM Magnesium acetate) and heated at 94° C. for 35 minutes and then chilled on ice. The fragmentation is confirmed by electrophoresis on agarose gel to verify the average size of the fragments. The fragmented, end-labeled cDNA is heat denatured before being on an identical array than the one used to screen the genomic DNA.

After hybridization and staining, the array is scanned and second hybridization pattern is obtained. Single nucleotide polymorphisms that are homozygous in the RNA but heterozygous in the genomic DNA are identified. These polymorphisms establish which genes are imprinted in an individual.

Example 2

Genotyping RNA

Five Lymphoblast cell lines from Coriell Institute were cultured and harvested. Total RNA was extracted from the cell lines followed by cDNA synthesis. After double stranded cDNA was obtained, cRNA was generated. The cRNA was labeled by incorporating biotinylated ribonucleotides into the cRNA during synthesis. The cRNA was then fragmented and hybridization onto the "TSC_0101_501 and 502" genotyping arrays. There are 4658 EcoRI SNPs tiled on the p502 array and 7398 XbaI SNPs tiled on the p501 array.

The cRNA was fragmented by adding 5× fragmentation buffer that contains $Mg^{2+}$ to break the phosphate bond and incubating at 94° C. for 35 minutes. Fragmented cRNA was mixed into expression or WGA hybridization cocktail. Expression hybridization cocktail contains (final concentration of): 0.05 µg/µl fragmented cRNA; 50 pM of control oligonucleotide B2; 0.1 mg/ml herring sperm DNA; 0.5 mg/ml acetylated BSA and 1× MES hybridization buffer. WGA hybridization cocktail contains (final concentration of): 0.05 µg/µl fragmented cRNA; 2.75 M TMA; 0.05 M MES hybridization buffer; 5% DMSO; 5 mM EDTA; 2.5× Denhardt's; 100 pM control oligonucleotide B2; 0.1 mg/ml herring sperm DNA; 0.01 mg/ml human cot-1 DNA and 0.01% tween-20.

After hybridization, arrays were washed, stained and scanned under expression or WGA conditions accordingly (for expression conditions see GeneChip® Expression Technical Manual, Affymetrix, Santa Clara, Calif. and for WGA conditions see U.S. patent application Ser. Nos. 10/264,945 and 60/417,190. Data from each cell line came from four hybridized arrays: two p501 arrays (one expression, one WGA) and two p502 arrays.

DNAs from the same five cell lines were purchased from Coriell Institute. WGA-FSP assay was carried out to amplify 400-800 by fragment from XbaI or EcoRI cut whole genomic DNA. The PCR products were then fragmented, labeled and hybridized onto TSC_0101_501 (XbaI) array or onto TSC_0101_502 (EcoRI) array and A/A+B was plotted where A is the signal corresponding to one allele and B is the signal corresponding to a second allele. For the genomic DNA samples signal from the sense strand, RAS1 was plotted against signal from the antisense strand RAS2. For the RNA only the sense signal, RAS1, could be analyzed.

Alternatively, double stranded cDNA made from the RNA may be hybridized to the array. This allows detection of both the sense and antisense signal as for the genomic DNA.

The results may be plotted on a graph of antisense signal versus sense signal. Genotypes may be represented as relative allele signals (RAS) on either one or both strands. RAS values are calculated from signals obtained for the A and B alleles for each SNP according to the formula A/A+B. An individual with an AA genotype would have a RAN value close to 1, an individual with a BB genotype will have a RAS value close to 0 and an individual with an AB phenotype will have a RAS value close to 0.5. Plotting RAS1 versus RAS2 should result in a diagonal with BB genotypes near (0,0), AB near (0.5, 0.5) and AA near (1,1). For a non-imprinted gene the genotypes of the SNP in the RNA should be similar to the genotypes of the SNP in the DNA. In some circumstances only RAS1 will be analyzed because RAS2 is the signal resulting from the opposite strand which isn't present in the RNA. The RNA may be converted to dsDNA and values for both RAS1 and RAS2 may be obtained. If the SNP is in an imprinted gene the RAS value for the RNA in a heterozygous individual will be close to either 1 or 0 (AA or BB) while the RAS values for the DNA will be close to 0.5 (AB).

The results of the example demonstrate that genotype information from the DNA is preserved in the RNA and also demonstrates the capability of genotyping RNA using genotyping arrays. In one of the individuals the DNA was found to be homozygous BB (RAS values close to 0) and the single corresponding RNA is also homozygous BB. In two individuals, the DNA is heterozygous AB (RAS values close to 0.5) and the corresponding RNA is also heterozygous AB (RAS1 value close to 0.5) indicating no imprinting. In one individual, the DNA is homozygous AA (RAS values close to 1) and the corresponding RNA is also homozygous AA (RAS1 value close to 1).

Conclusion

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of identifying at least one heterozygous gene showing monoallelic expression in an individual comprising
    assaying a genomic DNA sample from an individual to identify alleles of a heterozygous gene including a plurality of single nucleotide polymorphisms including at least 1,000 different polymorphic positions,
    assaying an RNA sample from the individual to determine whether RNA is transcribed from one or more of the alleles, whereby the heterozygous gene exhibits monoallelic expression when RNA is expressed from only one of the alleles.

2. The method of claim 1 wherein the at least one heterozygous gene showing monoallelic expression is an imprinted gene.

3. The method of claim 2 wherein parental origin of the expressed allele of the imprinted gene is determined by
    determining which alleles of the gene are present in the mother,
    determining which alleles of the gene are present in the father, and matching the expressed allele to one of the alleles present in the mother or the father.

4. The method of claim 1 wherein the gene showing monoallelic expression is a gene encoding a lymphoid-specific factor.

5. The method of claim 1 wherein the gene showing monoallelic expression is a subunit of an olfactory receptor.

6. The method of claim 1 wherein the gene showing monoallelic expression is a subunit of a T cell receptor.

7. The method of claim 1 wherein the gene showing monoallelic expression is a subunit of an immunoglobulin.

8. The method of claim 1 wherein the genomic DNA sample and the RNA sample are differentially labeled.

9. The method of claim 1 wherein the polymorphisms are associated with a phenotype.

10. The method of claim 1 wherein the polymorphisms are associated with a disease.

11. The method of claim 10 wherein the disease is cancer.

12. The method of claim 10 wherein the disease is a neurological disorder.

13. The method of claim 1 wherein the plurality of single nucleotide polymorphisms includes at least 10,000 different polymorphic positions.

14. The method of claim 1 wherein the plurality of single nucleotide polymorphisms includes at least 100,000 different polymorphic positions.

* * * * *